(12) United States Patent
Capcelea et al.

(10) Patent No.: US 8,515,557 B2
(45) Date of Patent: Aug. 20, 2013

(54) ELECTRODE ARRAY FOR A COCHLEAR IMPLANT

(75) Inventors: Edmond D. Capcelea, Bondi Junction (AU); Claudiu Treaba, Centennial, CO (US); Fysh Dadd, Lane Cove (AU)

(73) Assignee: Cochlear Limited, Macquarie University, NSW (AU)

( * ) Notice: Subject to any disclaimer, the term of this patent is extended or adjusted under 35 U.S.C. 154(b) by 123 days.

(21) Appl. No.: 12/743,804

(22) PCT Filed: Nov. 19, 2008

(86) PCT No.: PCT/AU2008/001718
§ 371 (c)(1),
(2), (4) Date: Oct. 29, 2010

(87) PCT Pub. No.: WO2009/065171
PCT Pub. Date: May 28, 2009

(65) Prior Publication Data
US 2011/0034969 A1    Feb. 10, 2011

(30) Foreign Application Priority Data
Nov. 19, 2007  (AU) ................................. 2007906334

(51) Int. Cl.
*A61N 1/05* (2006.01)
(52) U.S. Cl.
USPC ............................. 607/116; 607/55; 607/137
(58) Field of Classification Search
USPC ...................... 607/57, 55, 116, 137
See application file for complete search history.

(56) References Cited

U.S. PATENT DOCUMENTS

| | | | |
|---|---|---|---|
| 5,833,715 A * | 11/1998 | Vachon et al. | 607/120 |
| 6,548,313 B1 | 4/2003 | Ravi et al. | |
| 6,730,972 B2 | 5/2004 | Ravi et al. | |
| 7,162,308 B2 * | 1/2007 | O'Brien et al. | 607/116 |
| 7,221,982 B2 | 5/2007 | Aron et al. | |
| 7,240,416 B2 | 7/2007 | Milojevic et al. | |
| 7,596,415 B2 * | 9/2009 | Brabec et al. | 607/121 |
| 7,630,771 B2 * | 12/2009 | Cauller | 607/50 |
| 2004/0038251 A1 | 2/2004 | Smalley et al. | |
| 2004/0065559 A1 | 4/2004 | Iijima et al. | |

(Continued)

FOREIGN PATENT DOCUMENTS

| | | |
|---|---|---|
| EP | 01375429 | 1/2004 |
| EP | 01424095 | 6/2004 |

(Continued)

OTHER PUBLICATIONS

Zhang et al., "Strong, Transparent, Multifunctional, Carbon, Nanotube Sheets", Science, vol. 309, pp. 1215-1219, Aug. 19, 2005.

(Continued)

*Primary Examiner* — Joseph Stoklosa
(74) *Attorney, Agent, or Firm* — Kilpatrick, Townsend & Stockton, LLP.

(57) ABSTRACT

Disclosed is an electrode having a conducting wire and an electrode contact for a medical implant, the electrode being at least partially formed by Carbon Nanotubes (CNTs). Also disclosed are medical implants using the electrodes disclosed, as well as methods of manufacture of the electrode and medical implants. In one particular example, the electrode is formed with a CNT strand forming the conducting wire and a CNT sheet forming the electrode contact.

29 Claims, 8 Drawing Sheets

(56) References Cited

U.S. PATENT DOCUMENTS

| | | |
|---|---|---|
| 2004/0111141 A1 | 6/2004 | Brabec et al. |
| 2005/0075708 A1 | 4/2005 | O'Brien et al. |
| 2005/0203604 A1 | 9/2005 | Brabec et al. |
| 2006/0115409 A1 | 6/2006 | Li et al. |
| 2006/0129215 A1 | 6/2006 | Helmus et al. |
| 2007/0005117 A1 | 1/2007 | Fritsch et al. |
| 2007/0209093 A1 | 9/2007 | Tohji et al. |
| 2007/0225776 A1 | 9/2007 | Fritsch et al. |
| 2007/0255002 A1 | 11/2007 | Alba |
| 2008/0170982 A1 | 7/2008 | Zhang et al. |
| 2008/0203380 A1 | 8/2008 | Wang et al. |

FOREIGN PATENT DOCUMENTS

| | | |
|---|---|---|
| WO | 0071063 A1 | 11/2000 |
| WO | 00/76912 | 12/2000 |
| WO | 02/089907 A1 | 11/2002 |
| WO | 03/084869 | 10/2003 |
| WO | 2004/052447 | 6/2004 |
| WO | 2005/120823 | 12/2005 |
| WO | 2006105478 A2 | 10/2006 |
| WO | 2007/015710 | 2/2007 |
| WO | 2007/078082 | 7/2007 |
| WO | 2007087687 A1 | 8/2007 |
| WO | 2007/136404 | 11/2007 |
| WO | 2008/097333 | 8/2008 |
| WO | 2008/119138 | 10/2008 |

OTHER PUBLICATIONS

Zhang et al., "Multifunctional Carbon Nanotube Yarns by Downsizing an Ancient Technology" Science, vol. 306, pp. 1358-1361, Nov. 19, 2004.

Written Opinion of the International Searching Authority, International Application No. PCT/AU2008/001718, mailed Jan. 12, 2009.

International Searching Report, International Application No. PCT/AU2008/001718, mailed Jan. 12, 2009.

Meyyappan et al., "Carbon Nanotube Growth by PECVD: A Review", Plasma Sources Sci. Technol. 12 (2003) 205-216, Apr. 2, 2003 (12 pages).

\* cited by examiner

ELECTRODE ARRAY FOR A COCHLEAR IMPLANT

CROSS-REFERENCE TO RELATED APPLICATIONS

This application is a National Stage Application of International Application No. PCT/AU2008/001718, filed Nov. 19, 2008, entitled "ELECTRODE ARRAY FOR A COCHLEAR IMPLANT," which claims priority from Australian Provisional Patent Application No. 2007906334, filed Nov. 19, 2007. The contents of these applications are hereby incorporated by reference herein.

BACKGROUND

1. Field of the Invention

This invention relates to implants having electrodes and/or contacts for conducting electrical signals and/or delivering energy directly to one or more parts of a patient's body.

2. Related Art

The following publications are referred to in the present application and their contents are hereby incorporated by reference in their entirety: "Multifunctional Carbon Nanotube Yarns by Downsizing an Ancient Technology", Science Vol. 306. no. 5700, pp. 1358-1361; "Strong, Transparent, Multifunctional, Carbon Nanotube Sheets", Science Vol. 309. no. 5738, pp. 1215-1219); International Patent Application No. PCT/AU99/00391 (WO 00/71063 to Cochlear Limited); and U.S. Pat. No. 7,240,416 to Cochlear Limited.

Medical implants are used in many areas of medicine to enhance the length and/or quality of the life of the implant recipient. Such implants include pacemakers, controlled drug delivery implants and cochlear implants.

A cochlear implant allows for electrical stimulating signals to be applied directly to the auditory nerve fibers of the patient, allowing the brain to perceive a hearing sensation approximating the natural hearing sensation. These stimulating signals are applied by an electrode array implanted into the patient's cochlea.

The electrode array is connected to a stimulator unit which generates the electrical signals for delivery to the electrode array. The stimulator unit in turn is operationally connected to a signal processing unit which also contains a microphone for receiving audio signals from the environment, and for processing these signals to generate control signals for the stimulator.

The signal processing unit is in practice, located externally to the patient and the stimulator is implanted within the patient, usually near the mastoid on the patient's skull and underneath the surrounding tissue. The processor and stimulator may communicate by various wireless means including by a radio frequency link.

During insertion of the electrode, damage to the delicate structures of the patient's cochlea often occurs. This damage may cause a loss of any residual hearing.

Several methods have been proposed to reduce insertion trauma, including pre-curved electrode arrays and the use of insertion tools. However, these have not been particularly successful.

SUMMARY

According to one aspect of the present invention, there is provided a device for implanting into the body of a patient, the device comprising: a stimulator for converting an input signal to an electrical signal; at least one wire of an electrode electrically connected to the stimulator for receiving the electrical signal; and; an electrode contact of the electrode electrically connected to the at least one wire for operationally contacting a part of the body of the patient to deliver the electrical signal; wherein at least a portion of one of the at least one wire and/or the electrode contact is made from Carbon Nanotubes (CNTs).

According to a second aspect of the present invention, there is provided a method of manufacturing an electrode array for a medical implant, the method comprising: connecting a wire made at least partially from Carbon Nanotubes (CNTs) forming the conducting wire to an element made at least partially from Carbon Nanotubes (CNTs) forming the electrode contact.

According to a third aspect of the present invention, there is provided an electrode for a medical implant, the electrode comprising a conducting wire and an electrode contact, wherein at least a portion of one of the conducting wire and/or the electrode contact is made from Carbon Nanotubes (CNTs).

BRIEF DESCRIPTION OF THE DRAWINGS

Illustrative embodiments of the present invention are described herein with reference to the accompanying figures, in which.

DETAILED DESCRIPTION

The following describes a number of new techniques for manufacturing an electrode array using carbon nanotubes (CNTs), as well as an implantable medical lead for a cochlear implant comprising an electrode array that is manufactured according to the various techniques as described herein.

An electrode array will be understood to include one or more electrodes. Each electrode will be understood to include an electrode contact and an elongate element, such as a conductive filament or wire or strand of conductive filaments or wires (collectively referred to herein as wire) that is electrically connected to the electrode contact.

According to an embodiment, the electrodes are formed from at least one or more CNTs.

Certain embodiments of this invention will preferably have the following characteristics:

higher electrical conductivity than conventional electrode arrays (in one form, similar to, or better than Platinum (Pt) i.e., ~9.7*10^6 S/m, however, a lower conductivity may be suitable in other forms).

sufficient tensile strength to withstand the stresses placed upon the electrode array during the manufacture, transport, and handling of its lead.

sufficient flexibility to allow surgical insertion of its lead into a cochlea.

CNT spun wires and sheets are described, for example in the following documents, previously incorporated by reference: "Multifunctional Carbon Nanotube Yarns by Downsizing an Ancient Technology", Science Vol. 306. no. 5700, pp. 1358-1361 and "Strong, Transparent, Multifunctional, Carbon Nanotube Sheets", Science Vol. 309. no. 5738, pp. 1215-1219).

The CNT wires or sheets may be formed from SWCNT (Single Wall CNTs) or MWCNT (multiple wall CNTs).

CNT wires and/or sheets can be obtained from government research bodies such as the CSIRO (Commonwealth Scientific and Industrial Research Organisation) in Australia or from commercial companies including: Carbolex, Inc. in Ky., Lexington, USA; Carbon Nanotechnologies Incorporated in Houston Tex., USA; Thomas Swan & Co. Ltd in the United Kingdom; and Sun Nanotech Co Ltd in Nanchang, Jiangxi P.R. China.

Figure 1A:
FIG. 1A illustrates a Carbon Nanotube (CNT) strand or wire used in accordance with an embodiment of the present invention.
Figure 1B:
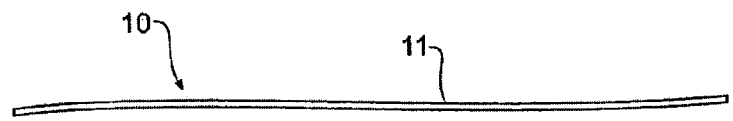
FIG. 1B illustrates the CNT strand or wire of FIG. 1A coated in an electrically insulating material, in accordance with an embodiment of the present invention.

Upon obtaining a supply of suitable CNT wire 1 (see FIG. 1A), each CNT wire is coated with a 1 to 5µm thick, outer electrically insulating barrier layer 11 (see FIG. 1B). This forms an insulated CNT wire 10 for use in the electrode array. Suitable materials for use in coating each wire include biocompatible polytetrafluoroethylene (PTFE), polyimide, polyurethane and Parylene. Each coated CNT wire 10 is then cut to a required length, usually in the order of between 200 mm to 300 mm.

Figure 1C:
FIG. 1C illustrates the coated strand or wire of FIG. 1B with a part of the coating removed to provide an exposed electrically conductive portion of the CNT strand or wire, in accordance with an embodiment of the present invention.

The insulating layer 11 is then removed from the ends of the wire 10, as shown in FIG. 1C. This may be achieved by exposing the ends to heat, or using laser ablation, mechanical abrasion, and/or any other suitable method so that a conductive portion of the wire 1 becomes exposed. For example, one suitable length of exposed conductive portion is 0.1 mm.

Figure 2:
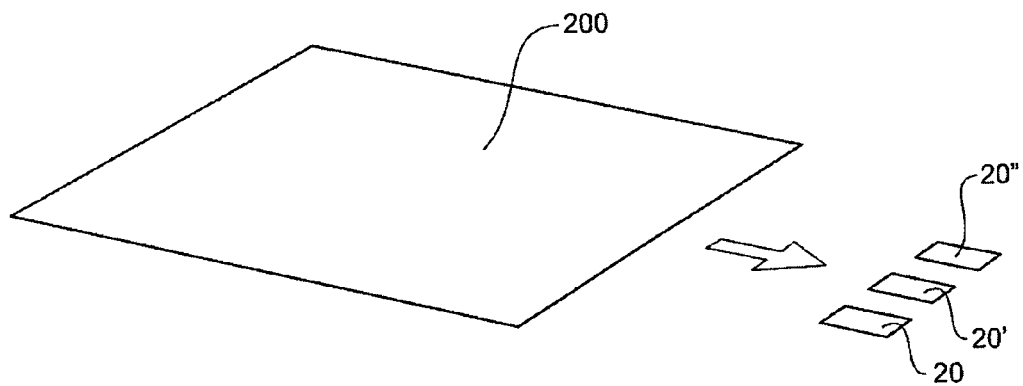
FIG. 2 illustrates a CNT sheet from which electrode contacts may be cut, in accordance with an embodiment of the present invention.

Next, upon obtaining a supply of CNT sheets 200, a number of discrete pieces are pressed or otherwise cut from the sheet to provide the CNT electrode contacts 20, 20', and 20", as shown in FIG. 2. An example of a cutting process that may be adapted for use in embodiments of the present invention is described in U.S. Pat. No. 7,240,416, also owned by the Applicant, the disclosure of which is incorporated herein in its entirety. The thickness of the CNT sheets can range between 1 to 100 microns. The size of each CNT electrode contact 20 is, for example, 0.3 mm wide×0.2 mm long, but may be varied according to the requirements of the particular application.

Forming the electrode array from CNT wires and/or sheets allows the size of each electrode and the thickness of the electrode array to be reduced in comparison with prior art manufacturing methods. Reducing the physical dimensions of each electrode allows the electrode array to be more flexible than those known previously in the art, without comprising on the strength required to withstand the stresses placed upon the electrode array during manufacture, transport, and handling of its lead. Furthermore, increasing the flexibility of the electrode array reduces the restoring force required to return a peri-modiolar designed cochlear implant lead to its original curved shape after being straightened prior to insertion of the lead into the cochlea, such that the thickness of the lead can be further reduced.

In accordance with embodiments of the present invention, the risk of insertion trauma and damage to residual hearing can be substantially reduced.

Each of the electrode contacts 20, 20', 20" is then placed in a holding jig, so that they may each be connected to a corresponding wire.

Figure 3A:
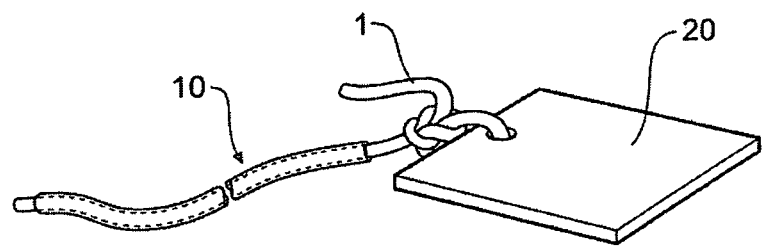
FIG. 3A illustrates one method of connecting the CNT strand or wire to an electrode contact, in accordance with an embodiment of the present invention.

FIG. 3A shows a method of joining one of the CNT electrode contacts 20 to an insulated CNT wire 10. The CNT electrode contact 20 is joined to the insulated CNT wire 10 by knotting the exposed end of wire 10 through an opening created in the contact 20 in such a way as to ensure that wire 1 is in electrical connection with electrode contact 20. Each opening is created during the initial pressing of the electrode contact 20. However, it is to be appreciated that the opening may be created in a further pressing or cutting step.

Figure 3B:
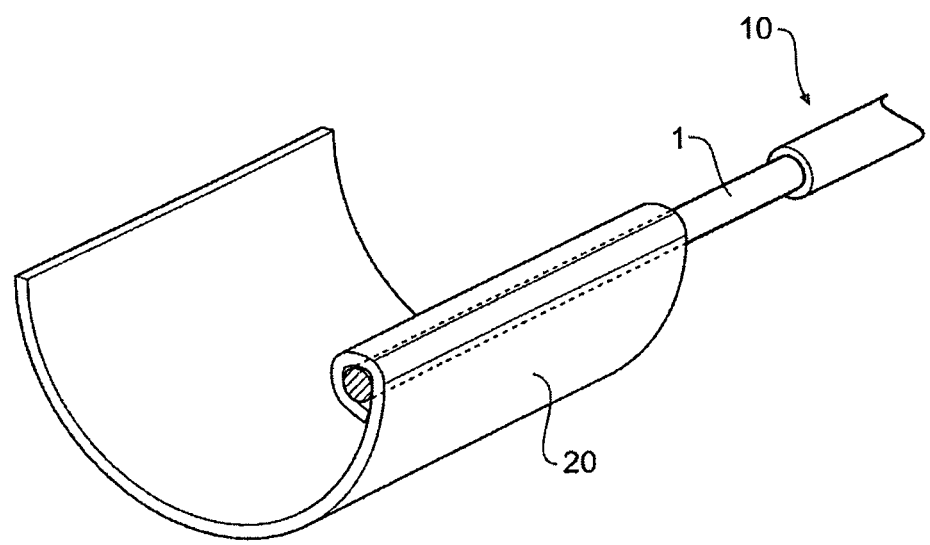
FIG. 3B illustrates another method of connecting the CNT strand or wire to the electrode contact, in accordance with an embodiment of the present invention.

Referring to FIG. 3B, an alternative arrangement provides the joining of an insulated CNT wire 10 to a conventional platinum electrode contact, instead of using a CNT electrode contact 20, as previously described. In this case, the conventional platinum electrode contact 20 is crimped around the exposed end of the CNT wire 10 to thereby retain the wire 1 in an electrically conductive connection with the electrode contact 20. Other joining methods that may also be used to electrically secure each wire 10 to its respective electrode contact 20 include gluing (with for example, conductive adhesive polymers), welding, or sewing.

Figure 8A:
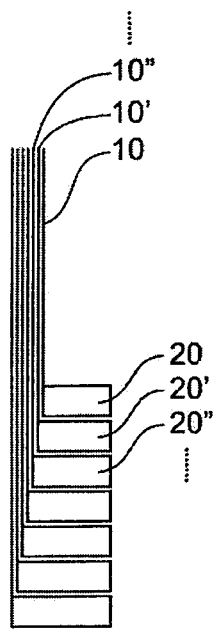
FIGS. 8A and 8B illustrates an array of electrodes of FIG. 7, in accordance with an embodiment of the present invention.
Figure 8B:
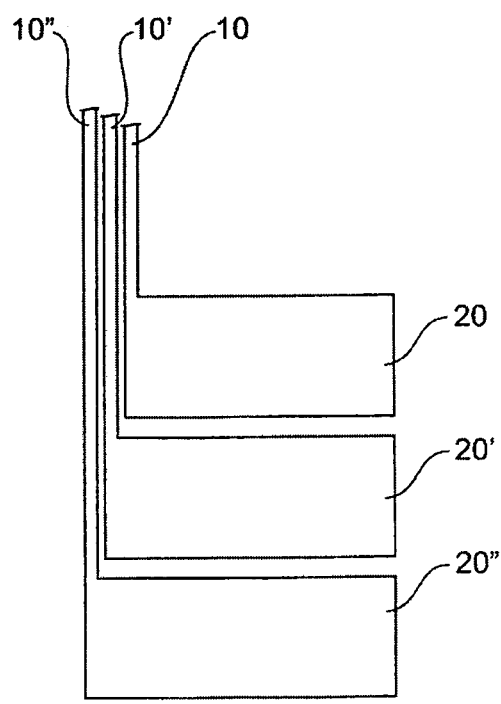

Alternatively, the elongate element and contact of the electrode is stamped or otherwise cut as a whole from the sheet of CNT material 200, such that no joining is required, as shown in FIGS. 8A and 8B.

Figure 4A:
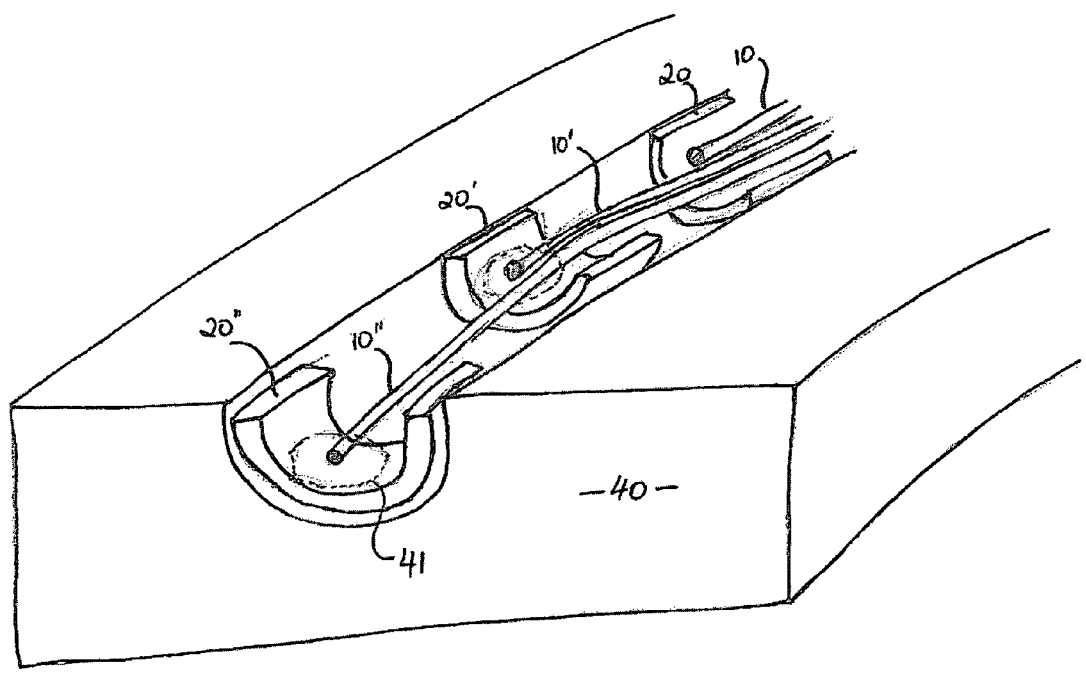
FIG. 4A illustrates the electrode array located within a U-shaped holding die.

In order to form the electrode array, the electrode contact 20, 20', 20" are placed in a U-shaped holding die 40, as shown in FIG. 4A. In this case, the electrode contacts 20, 20', 20" are welded or otherwise electrically connected to their respective wires 10, 10', 10" in sequential order, starting from the most proximal electrode contact 20, such that the wires 10', 10" are only placed over electrode contact 20 after it is welded to its respective wire 10. This is to avoid creating a short circuit between the wires 10, 10', 10" by inadvertently welding them together. Once all of the wires 10, 10', 10" have been connected to their respective electrode contacts 20, 20', 20", a droplet of adhesive 41, such as adhesive silicone, is placed in the trough of each electrode contact 20, 20', 20" in order to secure the wires 10, 10', 10" in place.

Figure 4B:
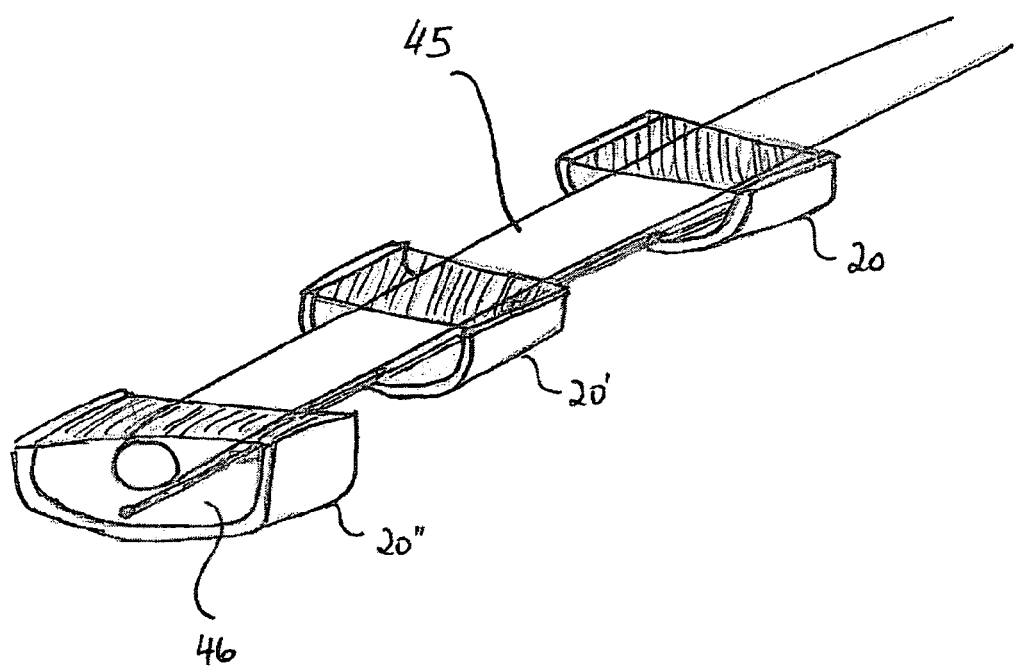
FIG. 4B—shows the assembled electrode array supported by a manufacturing stylet, in accordance with an embodiment of the present invention.

As shown in FIG. 4B, a production stylet 45 (for example, a PTFE coated wire) is suspended or otherwise placed over the electrode array before filling each trough with more silicone. The production stylet 45 is used to hold the electrode contacts 20, 20', 20" in spaced relationship to each other and provide further support to the electrode array, and is later removed to form a lumen in the lead. The holding die is then placed in an oven to cure the silicone.

It will be understood that electrode array arrangements need not use a stylet/lumen arrangement, and the various aspects of the invention are equally applicable to non-lumen/stylet arrangements.

Figure 5:
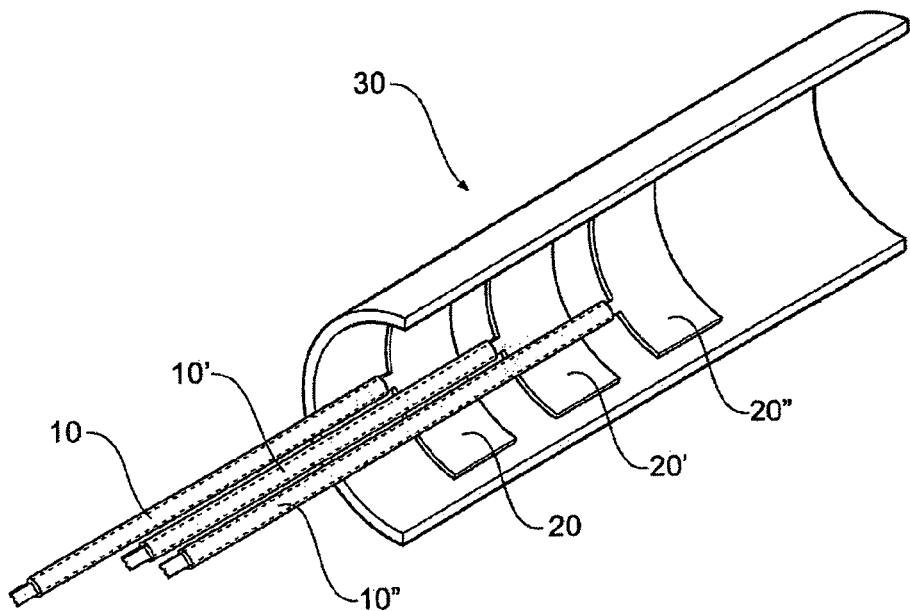
FIG. 5 illustrates a partial lead/electrode array assembly, in accordance with an embodiment of the present invention.

For example, the U-shaped holding die 40 can be flooded with silicone such that the electrode contacts 20, 20', 20" are supported in spaced relationship to each other by a partially-constructed lead body 30, as shown in FIG. 5.

Figure 6C:
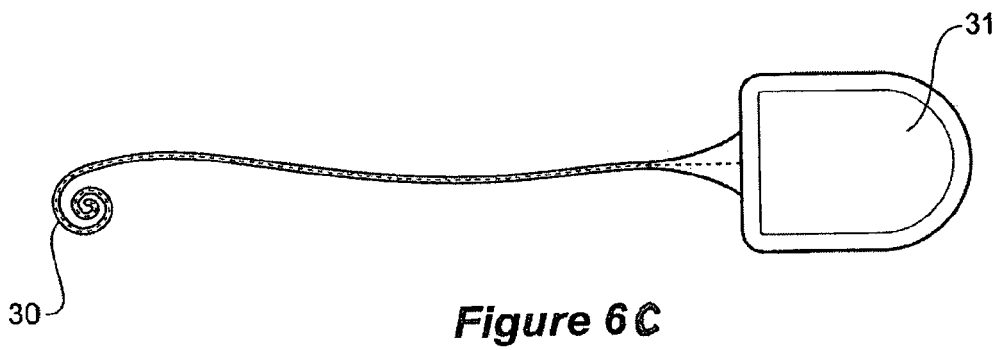
FIG. 6C illustrates one example of a lead/electrode array assembly in its completed form, in accordance with an embodiment of the present invention.
Figure 6A:
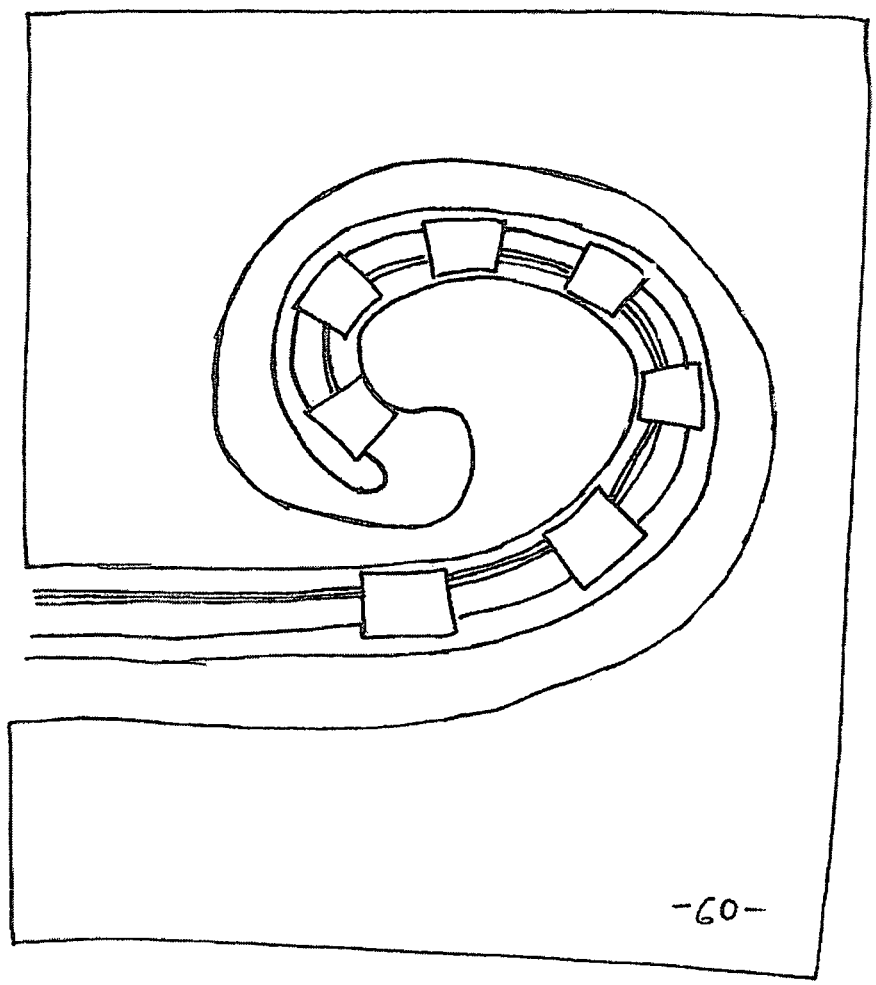
FIG. 6A illustrates a top view of the electrode array placed within a curved moulding die, in accordance with an embodiment of the present invention.
Figure 6B:
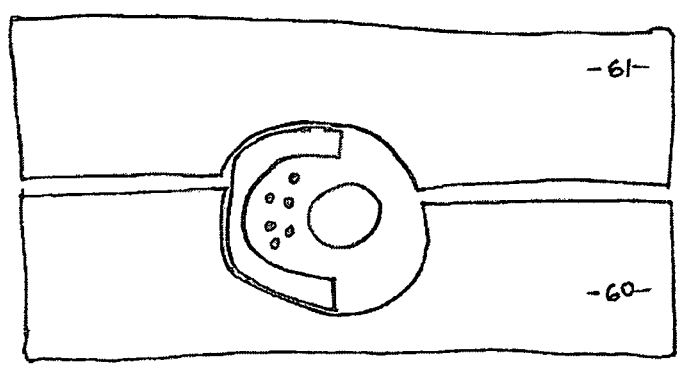
FIG. 6B illustrates a cross-sectional view of the electrode array placed within the curved moulding die of FIG. 6A, in accordance with an embodiment of the present invention.

The electrode array is then removed from the U-shaped holding die 40 and placed in a curved moulding die 60, as shown in FIG. 6A. The electrode array is positioned within the curved moulding die 60 such that the electrode contacts 20 are located along the medial side (inside of the curve) of the die 60. Then, the space in the die is packed with silicone material. A matching moulding die cover 61 is placed over the assembly and pressed down, as shown in FIG. 6B. The curved moulding die is then placed in an oven to cure the silicone, after which the electrode array is removed from the die 60. A similar method as described above for forming conventional electrode arrays is disclosed in International Patent Application No. PCT/AU99/00391 (WO 00/71063).

Dimensions of the intra-cochlear electrode array typically chosen for a cochlear implant electrode are 18 mm long. The length of the electrode array can range from 2 mm (for a short/basilar electrode) to 40 mm (a full length electrode). Other dimensions and shapes are also possible as would be understood by the person skilled in the art.

The electrode array described above forms the distal end of a lead/array assembly 30 that is adapted to be connected to an implantable cochlear stimulator (ICS) 31, as shown in FIG. 6C. The lead/array assembly 30 includes the electrode array, a helix section and a lead end to be connected to the ICS. The ICS is typically housed within a metallic case. The case has an array of feed through terminals corresponding to its multiple channels.

The CNTs can be connected to a standard feedthrough pin (platinum pins held in a ceramic layer) via crimping. More specifically, a notch can be cut into the platinum pin, the CNT conducting strand or wire placed in the notch and the pin then crimped around the CNT conducting strand or wire.

Other methods include tying and knotting the CNT conducting strand or wire onto the feedthrough pin, and then bending the pin down and over the tied CNT conducting strand or wire to lock the CNT conducting strand or wire to the pin, or using conductive adhesive polymers.

Yet another method is to arrange the CNT conducting strand or wires to match the feedthrough pins, embed them in an insulating epoxy (to provide mechanical support), cure the epoxy, polish a bottom side of the embedded strand or wires to expose the aligned CNT conducting strand or wires, and use conductive epoxy to attach the CNT conducting strand or wires to the feedthrough pins.

Moreover, there can be various sizes of electrode contacts. The limitations are based on physically fitting them into the body of the lead. Length of any one contact is dependant on the number of contacts (for example 1-256 contacts). The fewer the number of electrode contacts the larger the length can be, conversely, the higher the number the shorter the length. Width is dependant on the width of the electrode design and whether the electrode contact is flat, or wraps around the surface. In one example, 22 CNT electrode contacts are used. According to one aspect of the present invention however, far more electrodes (and corresponding electrode contacts and conducting strand or wires) may be used, including anywhere from 1 electrode to 256 or more electrodes, and more specifically, including 22 to 50 electrodes, 45 to 70 electrodes, 65 to 90 electrodes, 85 to 120 electrodes, 110 to 150 electrodes, 145 to 190 electrodes, 180 to 220 electrodes, 210 to 240 electrodes, 235 to 256 electrodes. It will also be understood that this includes electrode numbers greater than 256, including 257 to 300, 300 to 350, 350 to 400, 400 to 500, 500 to 600, 600 to 800, 800 to 1000 and above.

It will be appreciated that due to the very high surface area of contacts made out of CNT, the required size for effective electrical stimulation is reduced from that of contacts made from Platinum.

It will also be understood that various combinations of existing materials and structures may be used. For example, one alternative is to join the CNT conducting strand or wires to a traditional electrode contact, such as Platinum (Pt) or Platinum/Iridium (Pt/Ir). hi this case, the joining method may be as described above with reference to FIG. 3 or 4, including using knots, by crimping, or by using a conductive polymer adhesive.

In another alternative combination, 'traditional' wires (e.g. Pt or Pt/Ir) used as the conducting strand or wires may be joined to CNT electrode contacts. Again, the method of joining may be as described above.

In an alternative method of constructing an electrode array/lead assembly, a fine mesh, with square openings in the 5 to 10 micrometer range (for example) of biocompatible material, such as room temperature vulcanized (RTV) silicone, is glued on the outer surface of the electrode contacts. This is to hinder fibrous tissue growth on the outer surface of the electrode contact and/or to selectively stimulate only the growth of neuron cells on the outer surface of the electrode contacts.

Alternatively, the outer surface of the electrode contacts may be covered in a thin layer of silicone, and an ablation process used to create openings in the thin layer of silicone to expose the outer surface of the electrode contact. Suitable ablation processes include UV laser (193 run to 248 nm wavelength), ion beam etching, and mechanical and/or chemical polishing.

Alternatively, the outer surface of the electrode contacts may be finished (e.g. ground or pressed) or patterned (e.g. orientated corrugations) to achieve selective biological cell response.

In yet a further alternative, CNTs are deposited in channels formed in a suitable substrate matrix (e.g. silicone (PDMS) RTV matrix); the CNTs are mixed with a curable solution (e.g. PVA, Poly Vinyl Alcohol, a bio-compatible, water based glue) and poured into the channels in the matrix. An electrical field is applied to each channel to align the CNTs in electrical contact with each other, after which the solution is cured. CNT conductive structures are thus created in the substrate matrix. The matrix is sealed using an insulating barrier (e.g. parylene coating or RTV adhesive). Openings are created in the back of the substrate matrix to expose the CNT electrode contact area (for example, using an ablation process as described above), and a fine mesh (micrometer sized openings) of biocompatible material (such as RTV silicone) is deposited on top of the vertically grown CNT electrode contacts to hinder tissue growth on the contact surface and/or to selectively stimulate only the growth of neuron cells on the contact surface. A normal electrode array manufacturing process follows, as will be understood to the person skilled in the art.

In yet a further method of manufacture, the electrode contacts are made out of polyimide foil instead of CNT. After removing the electrode structure from the silicone injection die, the polyimide foil contacts are selectively removed (for example, using an ablation process as described above), thus exposing the non-insulated terminations of the CNT strand or wires in the array.

The array is placed and carefully positioned in a matching die that allows external access only in the area of the array formerly occupied by the polyimide contacts, and ensures surface protection of the rest of the array.

In the openings available on the back of the masking die above, CNT structures are vertically grown through a commercially available growth process such as PECVD (Plasma Enhanced Chemical Vapor Deposition). The CNT structures thus created are in intimate contact (low ohmic resistance) with the conductive CNT strand or wires in the electrode array; a suitable polymer, such as polyvinyl alcohol is deposited in the same openings and cured.

The masking die is removed and surface polishing is used to back trim/level the vertically grown CNT electrode contacts formed, back to the silicone surface of the electrode array. The thus formed CNT contacts may then be left unchanged or further covered with a conductive polymer (such as previously described). The array is placed back in the masking die and a fine mesh (5 to 10 micrometer size openings) of biocompatible material (such as RTV silicone, etc) is glued on top of the vertically grown CNT electrode contacts to hinder fibrous tissue growth on contact surface and/or selectively stimulate only the growth of neuron cells on the CNT electrode contact surface. A conventional electrode array manufacturing process follows.

Figure 7:
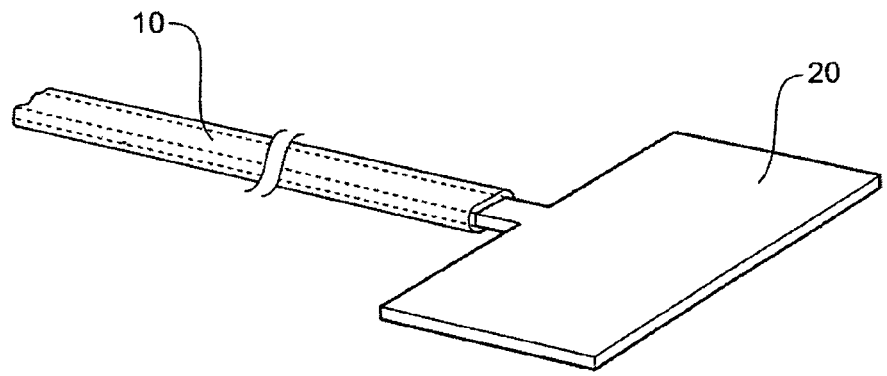
FIG. 7 illustrates an electrode strand or wire and contact produced, in accordance with an embodiment of the present invention.

In yet a further alternative arrangement, both the CNT conducting strand or wire 1 and the CNT electrode contact 20 are stamped from the CNT sheet 200 in a single operation. The CNT conducting strand or wires are coated with a 1 to 6 µm (for example) thick insulating barrier (e.g. Parylene-C) along then-length. FIG. 7 shows such a structure, with electrode contact 20 and insulated CNT 'wire' 10.

An example of a similar general technique is described in WO 02/089907, in the name of the Applicant of the present application, the entire contents of which are incorporated herein by reference. FIGS. 8A and 8B show an exemplary array of electrode/contact structures that may be constructed according to this method. FIG. 8A shows the array of CNT conducting strand or wires 10, 10', 10" with respective CNT electrode contacts 20, 20' and 20". FIG. 8B shows the connection between CNT conducting wires 10 and CNT electrode contacts 20 in more detail.

The resulting CNT conducting wire and CNT electrode contact structures are arranged in a moulding die in a pattern suitable for a functional electrode array. A biocompatible adhesive (e.g. silicone adhesive) is deposited on the backside of each CNT conducting strand or wire/CNT electrode contact and along (or at points along) the CNT wires' structure to ensure mechanical stability for subsequent manipulation.

While the various aspects of the present invention have been described with specific reference to a cochlear implant and having dimensions suitable for insertion into the cochlea, it will be understood that the principles of the invention may be applied to other types of implantable leads for applications other than cochlear stimulation. For example:

ABI (Auditory Brainstem Implant, electrode for hearing, placed in the brainstem) such as Cochlear Corporation's Nucleus 24 [R] Multichannel Auditory Brainstem Implant (Multichannel ABI).

Figure 9:
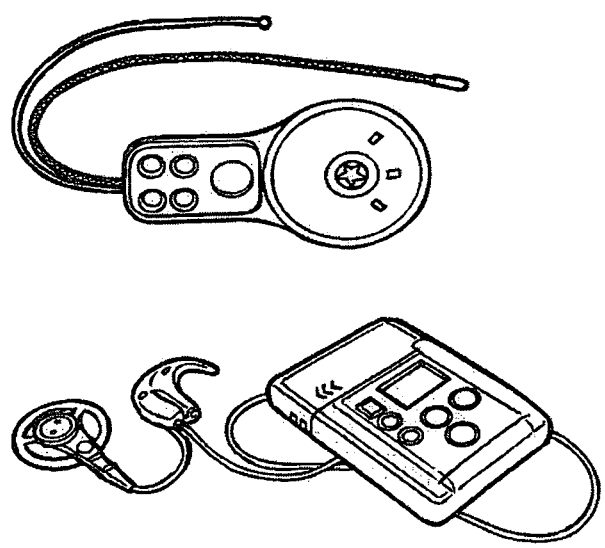
FIG. 9 illustrates an exemplary Auditory Brainstem Implant, in accordance with an embodiment of the present invention.

The auditory brainstem implant consists of a small electrode that is applied to the brainstem where it stimulates acoustic nerves by means of electrical signals. The stimulating electrical signals are provided by a signal processor processing input sounds from a microphone located externally to the patient. This allows the patient to hear a certain degree of sound. Examples of such implants are shown in FIG. 9.

FES (Functional Electrical Stimulation)

FES is a technique that uses electrical currents to activate muscles and/or nerves, restoring function in people with paralysis-related disabilities.

Injuries to the spinal cord interfere with electrical signals between the brain and the muscles, which can result in paralysis.

Figure 10:
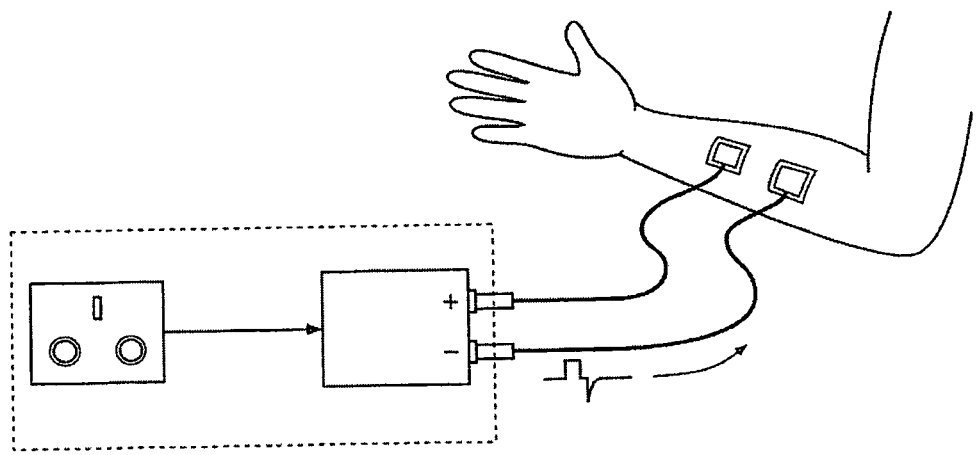
FIG. 10 illustrates an exemplary Functional Electrical Stimulation device, in accordance with an embodiment of the present invention.

It will be noted for clarity of illustration, the FES system shown in FIG. 10 is an external system. In an internal system the stimulator and leads and electrodes are all internal and the controller is external. In application with the present invention, the leads could be provided by CNT conducting strand or wires.

SCS (Spinal Cord Stimulator)

This system delivers pulses of electrical energy via an electrode in the spinal area and may be used for pain management. An example of a commercially available system is the RESTOREPRIME system by Medtronic, Inc, USA.

In another embodiment, a cochlear implant may be provided that is the same size as (or smaller or larger than) prior art implants, but that has a larger number of electrodes than prior art implants, thereby increasing the fineness of resolution of the coded frequencies and thus increasing effectiveness of the implant.

It will be understood that the above has been described with reference to a particular embodiment and that many variations and modifications may be made to the invention without departing from the scopes of the various aspects of the present invention.

It will also be understood that throughout this specification, unless the context requires otherwise, the words 'comprise' and 'include' and variations such as 'comprising' and 'including' will be understood to imply the inclusion of a stated integer or group of integers but not the exclusion of any other integer or group of integers.

The reference to any prior art in this specification is not, and should not be taken as, an acknowledgement or any form of suggestion that such prior art forms part of the common general knowledge.

The invention claimed is:

1. A device configured for implantation into a body of a patient, the device comprising:
    a stimulator for converting an input signal to an electrical signal;
    at least one wire of an electrode electrically connected to the stimulator for receiving the electrical signal; and
    an electrode contact of the electrode electrically connected to the at least one wire for operationally contacting a part of the body of the patient to deliver the electrical signal;
    wherein at least a portion of one of the at least one wire or the electrode contact is made from Carbon Nanotubes (CNTs), and the at least one wire is connected to the electrode contact by knotting an end of the conducting wire through a hole in the electrode contact.

2. The device of claim 1 wherein at least a portion of the at least one wire is made from the CNTs.

3. The device of claim 1 wherein at least a portion of the electrode contact is made from the CNTs.

4. The device of claim 1 wherein at least a portion of both the at least one wire and the electrode contact are made from the CNTs.

5. The device of claim 2 wherein the entire at least one wire is made from the CNTs.

6. The device of claim 3 wherein the entire electrode contact is made from the CNTs.

7. The device of claim 4 wherein the entire of both the at least one wire and the electrode contact are made from the CNTs.

8. The device of claim 7 wherein the at least one wire and the electrode contact are unitary.

9. The device of claim 1 wherein the device is a cochlear implant.

10. A method of manufacturing an electrode having a conducting wire and an electrode contact for a medical implant, the method comprising:
   connecting a wire made at least partially from Carbon Nanotubes (CNTs) forming the conducting wire to an element made at least partially from Carbon Nanotubes (CNTs) forming the electrode contact,
   wherein the CNT conducting wire is connected to the CNT electrode contact by knotting the CNT conducting wire through an opening in the CNT electrode contact.

11. The method of claim 10, further comprising coating the CNT conducting wire in an insulating material.

12. The method of claim 11 wherein the insulating material is polytetrafluoroethylene (PTFE).

13. The method of claim 10 wherein the electrode contact is formed from a CNT sheet.

14. The method of claim 13 wherein both the CNT conducting wire and the CNT electrode are formed from the CNT sheet.

15. The method of claim 11 further comprising processing at least one end of the coated CNT conducting wire to expose at least a portion of the CNT conducting wire.

16. The method of claim 15 wherein the step of processing involves heating.

17. The method of claim 10 further comprising attaching the CNT conducting wire to a further wire made from a material other than CNTs.

18. An electrode for a medical implant, the electrode comprising a conducting wire and an electrode contact, wherein at least a portion of one of the conducting wire or the electrode contact is made from Carbon Nanotubes (CNTs),
   wherein the conducting wire is connected to the electrode contact by knotting an end of the conducting wire through a hole in the electrode contact.

19. The electrode of claim 18 wherein at least a portion of the conducting wire is made from CNTs.

20. The electrode of claim 18 wherein at least a portion of the electrode contact is made from CNTs.

21. The electrode of claim 18 wherein at least a portion of both the conducting wire and the electrode contact are made from CNTs.

22. The electrode of claim 19 wherein the entire conducting wire is made from CNTs.

23. The electrode of claim 20 wherein the entire electrode contact is made from CNTs.

24. The electrode of claim 21 wherein the entire of both the conducting wire and the electrode contact are made from CNTs.

25. The electrode of claim 24 wherein the conducting wire and the electrode contact are unitary.

26. The device of claim 1, wherein the CNTs are single-wall CNTs or double-wall CNTs.

27. The device of claim 1, wherein the device further comprises an electrically insulating barrier layer coated onto the at least one wire.

28. The device of claim 27, wherein the electrically insulating barrier layer comprises at least one of biocompatible polytetrafluoroethylene, polyimide, polyurethane and parylene.

29. The device of claim 27, wherein the electrically insulating barrier layer comprises biocompatible polytetrafluoroethylene.

* * * * *